United States Patent
Xu et al.

(10) Patent No.: US 11,191,599 B2
(45) Date of Patent: Dec. 7, 2021

(54) FLEXIBLE SURGICAL TOOL SYSTEM AND A METHOD FOR CONTROLLING THE SAME WITH MOTION CONSTRAINTS

(71) Applicant: Beijing Surgerii Technology Co., Ltd., Bejing (CN)

(72) Inventors: Kai Xu, Beijing (CN); Jiangran Zhao, Beijing (CN); Zhengchen Dai, Beijing (CN); Zhixiong Yang, Beijing (CN); Zhijun Zhu, Bejing (CN); Bo Liang, Bejing (CN)

(73) Assignee: BEIJING SURGERII TECHNOLOGY CO., LTD., Beijing (CN)

(*) Notice: Subject to any disclaimer, the term of this patent is extended or adjusted under 35 U.S.C. 154(b) by 295 days.

(21) Appl. No.: 16/289,482

(22) Filed: Feb. 28, 2019

(65) Prior Publication Data

US 2019/0192239 A1    Jun. 27, 2019

Related U.S. Application Data

(63) Continuation of application No. PCT/CN2017/099846, filed on Aug. 31, 2017.

(30) Foreign Application Priority Data

Aug. 31, 2016 (CN) .......................... 201610796033.0

(51) Int. Cl.
*A61B 34/00* (2016.01)
*A61B 17/00* (2006.01)
(Continued)

(52) U.S. Cl.
CPC ........ *A61B 34/30* (2016.02); *A61B 17/00234* (2013.01); *A61B 17/29* (2013.01);
(Continued)

(58) Field of Classification Search
CPC ......... A61B 34/30; A61B 34/35; A61B 34/25; A61B 90/50; A61B 17/00234;
(Continued)

(56) References Cited

U.S. PATENT DOCUMENTS 8,839,798 B2 *  9/2014  Markowitz .......... A61B 5/0538
                                                            128/897
2013/0218172 A1    8/2013  Diolaiti
(Continued)

FOREIGN PATENT DOCUMENTS

CN       1533745 A    10/2004
CN     102018575 A     4/2011
(Continued)

OTHER PUBLICATIONS

International Search Report of PCT/CN2017/099846.
The first Office Action of CN application 2016107960330.
The search report of EP application 178454989.

*Primary Examiner* — Robert T Nguyen
(74) *Attorney, Agent, or Firm* — Bayes PLLC

(57) ABSTRACT

A flexible surgical tool system comprising a multi-degree-of-freedom mechanical arm, the flexible surgical tool, the remote control device and a controlling computer is provided. A method for controlling the same with motion constraints is also provided. The method can comprise: obtaining a target posture of the surgical actuator, a current posture of the surgical actuator and bending angle values of the sections of the flexible surgical tool. A desired velocity of the surgical actuator and a motion limitation condition can be obtained. Joint velocity of the multi-degree-of-freedom mechanical arm and bending velocity of the sections of the flexible surgical tool can be obtained. A target joint position value of the multi-degree-of-freedom mechanical arm, a target bending angular value of the sections of the flexible
(Continued)

surgical tool, and transmitting them to a corresponding controller to drive each section can be obtained. The above operations can be repeated.

20 Claims, 3 Drawing Sheets

(51) Int. Cl.
*A61B 17/29* (2006.01)
*A61B 34/30* (2016.01)
*A61B 34/35* (2016.01)
*A61B 90/50* (2016.01)

(52) U.S. Cl.
CPC ............ *A61B 34/25* (2016.02); *A61B 34/35* (2016.02); *A61B 90/50* (2016.02); *A61B 2017/00305* (2013.01); *A61B 2017/2905* (2013.01); *A61B 2034/305* (2016.02)

(58) Field of Classification Search
CPC ............ A61B 17/29; A61B 2034/305; A61B 2017/00305; A61B 2017/2905; A61B 34/76; A61B 2090/064; A61B 2034/301; B25J 9/1689; B25J 9/1607; B25J 9/1615; B25J 9/1653; B25J 9/1664
See application file for complete search history.

(56) References Cited

U.S. PATENT DOCUMENTS

| | | | |
|---|---|---|---|
| 2016/0000512 A1* | 1/2016 | Gombert | A61B 34/30 606/130 |
| 2016/0346054 A1* | 12/2016 | Hatakeyama | A61B 34/30 |
| 2019/0209241 A1* | 7/2019 | Begg | A61B 34/20 |
| 2020/0000367 A1* | 1/2020 | Oren | A61B 5/062 |
| 2020/0360100 A1* | 11/2020 | Mantri | A61B 90/37 |

FOREIGN PATENT DOCUMENTS

| | | |
|---|---|---|
| CN | 103200896 A | 7/2013 |
| CN | 104758055 A | 7/2015 |
| CN | 106361440 A | 2/2017 |
| WO | 2006124390 A2 | 11/2006 |
| WO | 2015142796 A1 | 9/2015 |

* cited by examiner

FLEXIBLE SURGICAL TOOL SYSTEM AND A METHOD FOR CONTROLLING THE SAME WITH MOTION CONSTRAINTS

CROSS-REFERENCE TO RELATED APPLICATIONS

The present application is a continuation of PCT Application No. PCT/CN2017/099846, filed on Aug. 31, 2017, which claims the priority to Chinese Patent Application No. 201610796033.0, entitled "A Flexible Surgical Tool System and A Method For Controlling The Same with Motion Constraints", filed on Aug. 31, 2016, the disclosure of which is incorporated herein by reference. The entire text thereof is incorporated herein by reference.

TECHNICAL FIELD

The invention relates to a medical instrument and a method for controlling the same, in particular to a flexible surgical tool system and a method for controlling the same with motion constraints.

BACKGROUND

Minimally invasive endoscopic surgery has occupied an important position in surgery due to its small trauma area and quick recovery. The robot-assisted endoscopic surgery greatly simplifies the doctor's operations while improving the operational accuracy. Existing Da Vinci surgical robots from Intuitive Surgical Inc. could assist doctors to complete the porous minimally invasive laparoscopic surgery and achieved a great commercial success. Compared with traditional rigid surgical instruments with limited bending degree of freedom achieved by the serial connection of rods, flexible surgical instruments could achieve further miniaturization and better motion performance, which is an important research direction for the development of next-generation minimally invasive laparoscopic surgical instruments.

In the course of robot-assisted minimally invasive endoscopic surgery, the surgical instrument is carried by a robotic or mechanical arm and enters into the body of a patient through a sheath secured to a skin incision to complete the surgical procedure. During a surgical procedure, the effects of the motion of the surgical instrument on the spatial position of the sheath shall be reduced in the maximum degree so as to minimize the pulling to the skin incision. Therefore, a robot-assisted laparoscopic surgical system needs to perform a surgical procedure while satisfying the above-described motion constraints. Existing solutions often use a mechanical structure design (e.g. Remote Center of Motion (RCM)) mechanism to satisfy the above motion constraints, and thus, the flexibility of use is poor.

SUMMARY OF THE INVENTION

In view of the above problems, an object of the present invention is to provide a method for controlling a flexible surgical tool system with motion constraints, which can achieve the agile control of the surgical tool system with the sheath-constraints of motion without using a dedicated remote motion center mechanism.

Another object of the present invention is to provide a flexible surgical tool system that can be preferably applied to a single-hole minimally invasive laparoscopic surgical robotic system via a single surgical incision or to a porous laparoscopic surgical robotic system.

In order to achieve the above objects, the present invention adopts the following technical solution: a method of controlling a flexible surgical tool system with motion constraints, the method comprising the following steps: 1) setting up a flexible surgical tool system that includes a multi-degree-of-freedom mechanical arm, a flexible surgical tool, a remote control device, and a controlling computer; the flexible surgical tool includes a flexible surgical tool driving unit, an outer sleeve, a flexible multi-section arm body, and a surgical actuator; 2) transmitting, by the remote control device, a remote control device status signal to the controlling computer, the controlling computer receives the remote control device status signal and calculates the target posture of the surgical actuator according to the conversion of the registration and mapping relationships; 3) receiving, by the controlling computer, the joint position values of the multi-degree-of-freedom mechanical arm fed back by the multi-degree-of-freedom mechanical arm and the bending angle value of the sections of the flexible surgical tool fed back by the flexible surgical tool, respectively, and uses a robotic forward kinematics model to obtain the current posture of the surgical actuator based on the multi-degree-of-freedom mechanical arm and the mechanical structure of the surgical tool; 4) calculating, by the controlling computer, a desired velocity of the surgical actuator according to the target posture of the surgical actuator and the current posture of the flexible surgical actuator; 5) calculating, by the controlling computer, the current position of the sheath relative to the outer sleeve using the robotic forward kinematics model according to the joint position values of the multi-degree-of-freedom mechanical arm, the bending angle value of the sections of the flexible surgical tool and the spatial position of the sheath; 6) obtaining the motion limitation condition applied by the sheath to the outer sleeve based on the current position of the sheath relative to the outer sleeve; according to the motion limitation condition and the desired velocity of the surgical actuator, applying inverse kinematics algorithm with multi-priority-object to calculate a joint velocity of the multi-degree-of-freedom mechanical arm and a bending velocity of the sections of the flexible surgical tool; 7) calculating a target joint position value of the multi-degree-of-freedom mechanical arm based on the joint velocity of the multi-degree-of-freedom mechanical arm and a preset control loop time, and transmitting the same to the controller of the multi-degree-of-freedom mechanical arm to drive individual joints; 8) calculating a target bending angle value of the sections of the flexible surgical tool according to the bending velocity of the sections of the flexible surgical tool and the control loop time, and transmitting it to the controller of the flexible surgical tool to drive the respective sections; 9) ending the control loop and repeating the operations from step 2) to step 8).

Preferably, in the step 4), the desired velocity of the surgical actuator is calculated as follows:

$$\dot{x} = \begin{bmatrix} v \\ \omega \end{bmatrix} = \begin{bmatrix} v_{lim}(p_t - p_c)/\|p_t - p_c\| \\ \omega_{lim} rot_r^{-1}(R_t R_c^T) \end{bmatrix},$$

In the formula, $\dot{x}$ is the velocity vector of the surgical actuator, including a linear velocity vector $v$ and an angular velocity vector $\omega$; $p_t$ is the target position of the surgical actuator, i.e. the position vectors included in the target posture of the surgical actuator; $R_t$ is the rotation matrix of the target posture of the surgical actuator, i.e. the posture matrix included in the target posture of the surgical actuator; $p_c$ is the current position of the surgical actuator, i.e. the position vector included in the current posture of the surgical actuator; $R_c$ is the rotation matrix of the current posture of the surgical actuator, i.e. the posture matrix included in the current posture of the surgical actuator; $v_{lim}$ is the linear velocity limitation value of the surgical actuator; $\omega_{lim}$ is the angular velocity limitation value of the surgical actuator; $\text{rot}_{\hat{r}}^{-1}(R_r R_c^T)$ is the unit vector of the rotational axis required to rotate from the current posture of the surgical actuator to the target posture of the surgical actuator; $\hat{r}$ denotes that the $\text{rot}_{\hat{r}}^{-1}(R_r R_c^T)$ is a unit vector.

Preferably, in the step 5), the spatial position of the sheath is the spatial position where the sheath is fixed to the surgical incision.

Preferably, in the step 6), the motion limitation condition is that the velocity direction of the outer sleeve at a particular fixed point in the sheath shall be consistent with a tangential direction of the channel axis for passing through the outer sleeve at the particular fixed point; said particular fixed point is the intersection point of the channel axis for passing through the outer sleeve in the sheath with the skin incision.

Preferably, in the step 6), the inverse kinematics algorithm with the multi-priority-object is:

$$C = H\dot{q} \quad C = v_{RCM\perp} = 0$$

$$\dot{x} = J\dot{q}$$

$$\dot{q} = (I - H^+H)(J(I - H^+H)) + \dot{x}$$

In the formula, C is the motion limitation condition; H is the Jacobian matrix of the motion limitation condition; $\dot{q}$ is a vector consisting of the joint velocity of the multi-degree-of-freedom mechanical arm and the bending velocity of the sections of the flexible surgical tool; $v_{RCM\perp}$ is a velocity vector in a direction at which the outer sleeve is at a particular fixed point in the sheath, the direction is the tangential direction of the particular fixed point that is perpendicular to the channel axis of the outer sleeve; $\dot{x}$ is the desired velocity vector for the surgical actuator; J is the Jacobian matrix for surgical actuators.

A flexible surgical tool system for implementing the above controlling method, characterized in that the system comprises a multi-degree-of-freedom mechanical arm, a flexible surgical tool, a remote control device and a controlling computer; the remote control device exchanges information with the controlling computer, the remote control device transmits desired control information for the multi-degree-of-freedom mechanical arm and the flexible surgical tool to the controlling computer; the controlling computer exchanges information with the multi-degree-of-freedom mechanical arm and the flexible surgical tool, respectively, transmits control signals to the multi-degree-of-freedom mechanism arm and the flexible surgical tool, respectively, and receives a current status fed back by the multi-degree-of-freedom mechanism arm and the flexible surgical tool, respectively, the current status includes motion postures of the multi-degree-of-freedom mechanical arm and the flexible surgical tool and information about the external disturbance encountered; the controlling computer returns the received information (after being processed) to the remote control device, and the remote control device outputs an acting force to reflect the latent degree of movements of the multi-degree-of-freedom mechanical arm and the flexible surgical tool or the information about the external disturbance encountered; said control signal is transmitted on a connection constructed by the Ethernet.

Preferably, the multi-degree-of-freedom mechanical arm is equipped with a mechanical arm controller for receiving a control signal from the Ethernet and then transmitting it to the motor driver through the controller LAN bus to drive the corresponding motor; each of the joints of the multi-degree-of-freedom mechanical arm is equipped with a rotation angle sensor for detecting the joint position values of multi-degree-of-freedom mechanical arm in real time, and transmitting them, via the controller LAN bus, to the mechanical arm controller in the form of a feedback signal, the mechanical arm controller transmits the feedback signal, over the Ethernet, to the controlling computer so as to perform the calculation of the control loop.

Preferably, the flexible surgical tool is provided with a flexible surgical tool controller, which receives a control signal from the Ethernet and transmits it to the motor driver through the controller LAN bus to drive the corresponding motor; the output axis of each motor in the flexible surgical tool is equipped with a rotation angle sensor, which transmits the rotation angle of the output axis measured in real time, via a the controller LAN bus, to the flexible surgical tool controller in the form of a feedback signal, the flexible surgical tool controller executes the forward kinematic algorithm to obtain a bending angle value of the sections of the flexible surgical tool and transmits it in the form of a feedback signal, via the Ethernet, to the controlling computer for the calculation of the control loop.

Preferably, the controlling computer transmits the control signals, via a LAN bus, to the respective joint motor drivers of the multi-degree-of-freedom mechanical arm and the flexible surgical tool in a broadcast manner, the respective joint motor drivers in the multi-degree-of-freedom mechanical arm and the flexible surgical tool selectively read a corresponding control signal so as to drive the corresponding motor; each of the joints of the multi-degree-of-freedom mechanical arm and the output axis of each of the motors in the flexible surgical tool are equipped with a rotation angle sensor.

Preferably, the flexible surgical tool is fixed at the end of the multi-degree-of-freedom mechanical arm, the multi-degree-of-freedom mechanical arm has a plurality of degrees of freedom; the flexible surgical tool comprises a flexible surgical tool drive unit, an outer sleeve, a flexible multi-section arm body and a surgical actuator; the surgical actuator is a mechanical, energy or sensory surgical actuator that is fixed to the end of the flexible multi-section arm body, one end of the flexible multi-section arm body is guided by the outer sleeve to be connected into the flexible surgical tool drive unit; in use, the outer sleeve passes through a sheath that is fixed at the skin incision.

The invention adopts the above technical solutions, and has the following advantages: the invention comprises a multi-degree-of-freedom mechanical arm, a flexible surgical tool, a remote control device and a controlling computer; information is exchanged with the controlling computer via the remote control device; the controlling computer exchanges information with the multi-degree-of-freedom mechanical arm and the flexible surgical tool, respectively; the carry of the multi-degree-of-freedom mechanical arm is implemented and the posture of the flexible surgical tool is changed with the constraint of the sheath movements; with the precise bending of the flexible arm body of the flexible surgical tool in any direction, the agile movement of the distal surgical actuator of the flexible surgical tool is achieved.

DRAWINGS

DETAILED DESCRIPTION

Figure 1:
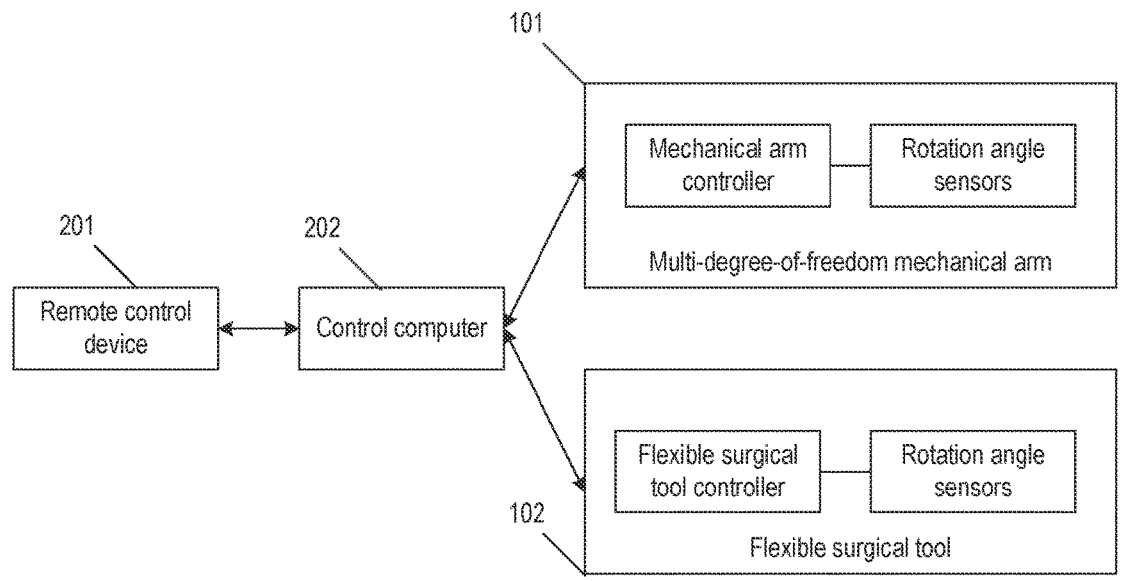
FIG. 1 is a schematic view showing a controlling architecture of a flexible surgical tool system of the present invention.

The preferred embodiments of the present invention will be described in detail with reference to the accompanying drawings. The embodiment shown in the drawings are not intended to limit the scope of the invention, but only to illustrate the spirit of the invention.

As shown in FIG. 1, the present invention provides a flexible surgical tool system that includes a multi-degree of freedom mechanical arm 101, a flexible surgical tool 102, a remote control device 201 and a controlling computer 202. The remote control device 201 performs information exchange with the controlling computer 202, the remote control device 201 transmits desired control information for the multi-degree-of-freedom mechanical arm 101 and the flexible surgical tool 102 to the controlling computer 202; the controlling computer 202 exchanges information with the multi-degree-of-freedom mechanical arm 101 and the flexible surgical tool 102, respectively, the controlling computer 202 transmits control signals to the multi-degree-of-freedom mechanical arm 101 and the flexible surgical tool 102, respectively, and receives the current status fed back by the multi-degree-of-freedom mechanical arm 101 and the flexible surgical tool 102, the current status includes, but is not limited to, the motion postures of the multi-degree-of-freedom mechanical arm 101 and the flexible surgical tool 102 and information about the external disturbance encountered, the controlling computer 202 processes the received information and returns it to the remote control device 201, the remote control device 201 outputs a certain acting force to reflect the latent degree of movements of the multi-degree-of-freedom mechanical arm 101 and the flexible surgical tool 102 or the information about the external disturbance encountered. Preferably, the aforementioned control signals are transmitted over a connection constructed by Ethernet.

In the above embodiments, the multi-degree-of-freedom mechanical arm 101 is equipped with a mechanical arm controller for receiving a control signal from the Ethernet and then transmitting it to the motor driver through the controller LAN bus (CAN) to drive the corresponding motor, and thus to drive the action of the multi-degree-of-freedom mechanical arm 101; each of the joints of the multi-degree-of-freedom mechanical arm 101 is equipped with a rotation angle sensor for detecting the joint position values 303 of the multi-degree-of-freedom mechanical arm in real time, and transmitting them, via the controller LAN bus (CAN), to the mechanical arm controller in the form of a feedback signal, the mechanical arm controller transmits the feedback signal (including the joint position values 303 of the multi-degree-of-freedom mechanical arm), over the Ethernet, to the controlling computer 202 so as to perform the calculation of the control loop.

In the above embodiments, the flexible surgical tool 102 is provided with an embedded computer based on an ARM chip, which is a flexible surgical tool controller, and the embedded computer receives a control signal from the Ethernet, and then transmits it, via the controller LAN bus (CAN), to the motor drive to drive the corresponding motor, and thus drive the flexible surgical tool 102. The output axis of each motor of the flexible surgical tool 102 is equipped with a rotation angle sensor, which transmits the rotation angle of the output axis measured in real time, via a the controller LAN bus (CAN), to the flexible surgical tool controller in the form of a feedback signal, the flexible surgical tool controller executes the forward kinematic algorithm to obtain a bending angle value 304 of the sections of the flexible surgical tool and transmits it in the form of a feedback signal, via the Ethernet, to the controlling computer 202 for the calculation of the control loop.

In a preferred embodiment, neither the multi-degree-of-freedom mechanical arm 101 nor the flexible surgical tool 102 has a separate controller. Preferably, the controlling computer 202 transmits all joint control signals to the respective joint motor drivers of the multi-degree-of-freedom mechanical arm 101 and the flexible surgical tool 102 in a broadcast manner via the controller area network bus (CAN). Each of the joint motor drivers in the multi-degree-of-freedom mechanical arm 101 and the flexible surgical tool 102 selectively read the corresponding control signals for driving the respective motors. Similarly, the rotation angle sensor in the multi-degree-of-freedom mechanical arm 101 transmits the joint position value 303 of the multi-degree-of-freedom mechanical arm detected in real time, via the controller LAN bus (CAN), in the form of a feedback signal to the controlling computer 202 for the calculation of the control loop; the rotation angle sensor in the flexible surgical tool 102 transmits the real-time measured rotation angle of the output axis to the controlling computer 202 via a controller LAN bus (CAN) in the form of a feedback signal, and the controlling computer 202 performs a forward kinematics algorithm to obtain a bending angle value 304 of the sections of the flexible surgical tool, and thus perform the calculation of the control loop.

Figure 2A:
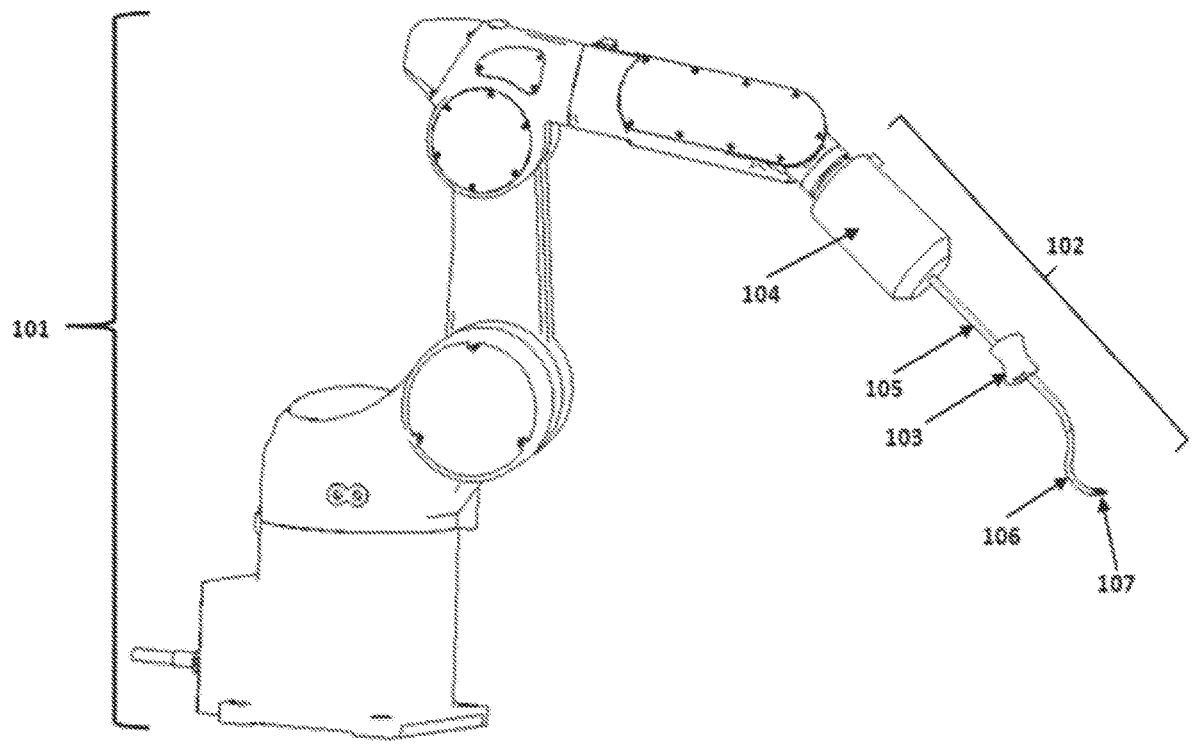
FIG. 2a is a schematic structural view of the flexible surgical tool system of the present invention.
Figure 2B:
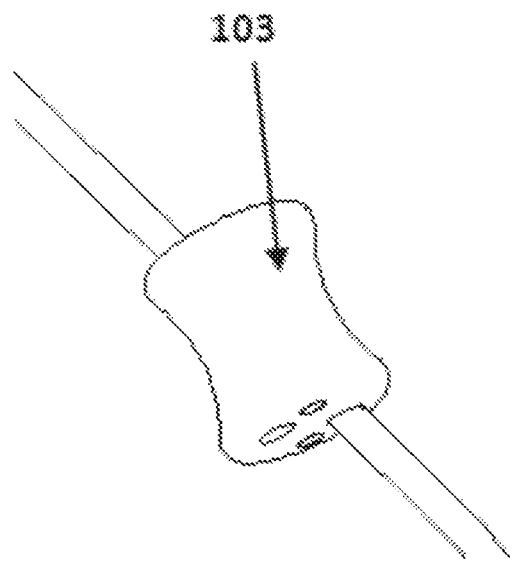
FIG. 2b is a schematic structural view showing a sheath having a plurality of channels in the flexible surgical tool system of the present invention.
Figure 2C:
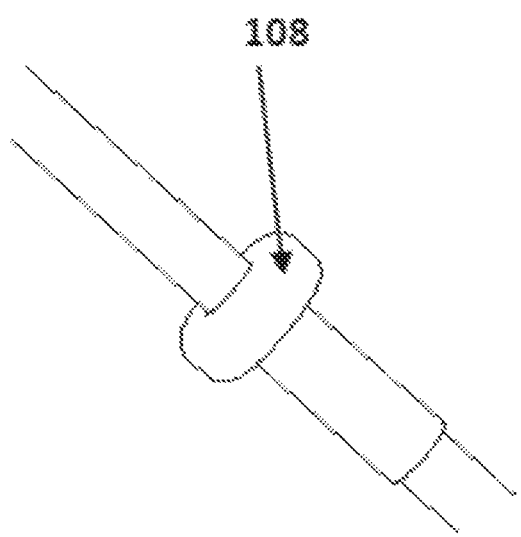
FIG. 2c is a schematic structural view of a single-channel sheath of the flexible surgical tool system of the present invention.

As shown in FIGS. 2a-2c, the flexible surgical tool 102 is fixed to the end of the multi-degree-of-freedom mechanical arm 101; the multi-degree-of-freedom mechanical arm 101 has a plurality of degrees of freedom (usually greater than or equal to six), and the equipment with the flexible surgical tool 102 achieves a large spatial range of posture transformation. The flexible surgical tool 102 includes a flexible surgical tool drive unit 104, an outer sleeve 105, a flexible multi-section arm body 106 and a surgical actuator 107. The surgical actuator 107 is secured to the end of the flexible multi-section arm body 106, one end of the flexible multi-section arm body 106 is guided by the outer sleeve 105 to be connected into the flexible surgical tool drive unit 104; in the present embodiment, the outer sleeve 105 can be a straight tube or a curved rigid pipe of arbitrary curve, the front section thereof is a rigid straight tube, and the rear section thereof is a rigid arc-shaped elbow. The outer sleeve 105 passes through the sheath 103 that is fixed at the skin incision, the sheath 103 has a plurality of channels and provides channels to the instruments (typically three surgical tools and an imaging illumination tool) required for single-hole laparoscopic surgery, wherein the surgical tool channel is an inclined channel, which not only allows the feeding of the outer sleeve and the rotational movement about its own axis, but also does not limits the deflection movement of the outer sleeve 105 in any direction centered in the spatial position of the sheath. In use, the multi-degree-of-freedom mechanical arm 101 carries the flexible surgical tool 102, such that the surgical actuator 107, the flexible multi-section arm body 106, and a portion of the outer sleeve 105 enter into the patient's body through the channel provided by the sheath 103. When the outer sleeve 105 is a pre-bent sleeve, it helps to form a triangular-arched surgical posture through the plurality of flexible multi-section arm bodies 106 of the sheath 103 in the initial straight state, thereby implements single-hole laparoscopic surgery.

In use, the multi-degree-of-freedom mechanical arm 101 can achieve a wide range of motion of the flexible surgical tool 102. The flexible surgical tool 102 can achieve a small range of precise and flexible movement of the flexible multi-section arm body 106 in the patient's body and the driving of the surgical actuator 107. It should be noted that when the multi-degree-of-freedom mechanical arm 101 carries the flexible surgical tool 102 for surgical operation, it is necessary to ensure that the outer sleeve 105 in the flexible surgical tool 102 is in the channel provided by the sheath 103 fixed at the skin incision, the outer sleeve 105 always makes deflection movement around a particular fixed point (i.e. the sheath 103 or the intersection of the channel axis, for passing through the outer sleeve 105, in the sheath 108 with the skin incision), and only generates linear feeding movement along the axial direction of the channel and a rotational movement about the axis, so as to avoid pulling produced by the outer sleeve 105 together with the sheath 103 on the skin incision during a surgical procedure.

In a preferred embodiment, as shown in FIG. 2, the outer sleeve 105 shown in this embodiment is a rigid straight sleeve, which can pass through a sheath 108 that includes only one channel, and the sheath 108 is also fixed to the skin incision. The outer sleeve 105, the flexible multi-section arm body 106 and the surgical actuator 107 in the flexible surgical tool system also can pass through the plurality of the sheaths 108, and thus implement porous laparoscopic surgery.

In the above embodiments, the surgical actuator 107 may be a mechanical surgical actuator, such as forceps, scissors, hemostats and the like; the surgical actuator 107 may also be an energy type surgical actuator, such as electric knife, electrocoagulation head and the like; the surgical actuator 107 can also be a force sensor component that measures the external disturbances on the surgical actuator 107 itself. The surgical actuator 107 is fixed to the end of the flexible multi-section arm body 106. The flexible multi-section arm body 106 has one or more flexible sectional structures that can be bent in an arbitrary direction, and the bending in an arbitrary direction of each flexible sectional structure can be parameterized with the bending angle values of the sections of the flexible surgical tool. The bending angle values of the sections of the flexible surgical tool include bending plane pointing angle values of the flexible sectional structures and the bending angle values in the bending plane.

In the above embodiments, the flexible surgical tool driving unit 104 includes a mechanical transmission structure and a motor driver, and the like, and can realize motion driving of the flexible multi-section arm body 106 and the surgical actuator 107.

Figure 3:
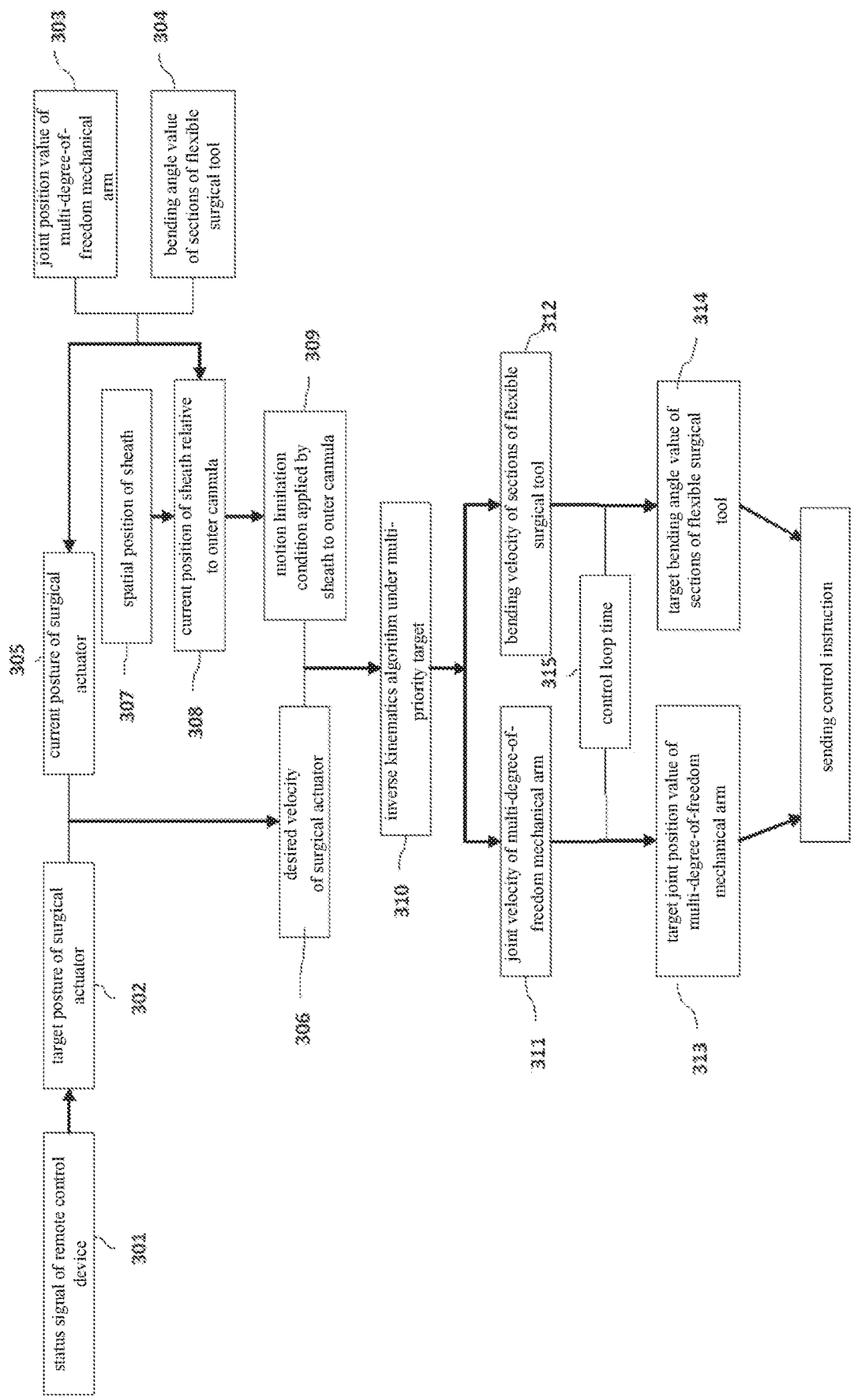
FIG. 3 is a flow chart showing a method of controlling the flexible surgical tool system of the present invention with motion constraints.

As shown in FIG. 3, the present invention is based on the above flexible surgical tool system, and also provides a method of controlling the flexible surgical tool system with motion constraints, the loop control is achieved by the controlling computer 202, which includes the following steps:

1) transmitting, by the remote control device 201, the status signal 301 of the remote control device to the controlling computer 202, wherein the status signal 301 of the remote control device is received by the controlling computer 202, and the target posture 302 of the surgical actuator is obtained according to the conversion of the registration and mapping relationship;

wherein, the status signal 301 of the remote control device includes the desired position and pointing signals of the surgical actuator 107;

2) receiving, by the controlling computer 202, the joint position values 303 of the multi-degree-of-freedom mechanical arm fed back by the multi-degree-of-freedom mechanical arm 101 and the bending angle value 304 (i.e. the bending angle value of the respective sectional structures) of the sections of the flexible surgical tool fed back by the flexible surgical tool 102, respectively, and using a robotic forward kinematics model to calculate the current posture 305 of the surgical actuator 107 based on the multi-degree-of-freedom mechanical arm 101 and the mechanical structure of the flexible surgical tool 102;

3) calculating, by the controlling computer 202, a desired velocity 306 (including the linear velocity and angular velocity) of the surgical actuator according to the target posture 302 of the surgical actuator and the current posture 305 of the surgical actuator.

The specific algorithm is as follows:

$$\dot{x} = \begin{bmatrix} v \\ \omega \end{bmatrix} = \begin{bmatrix} v_{lim}(p_t - p_c)/\|p_t - p_c\| \\ \omega_{lim} rot_{\hat{r}}^{-1}(R_t R_c^T) \end{bmatrix},$$

In the formula, $\dot{x}$ is the velocity vector of the surgical actuator 107 (i.e. the desired velocity 306 of the surgical actuator) including a linear velocity vector $v$ and an angular velocity vector $\omega$; $p_t$ is the target position of the surgical actuator, i.e. the position vector included in the target posture 302 of the surgical actuator; $R_t$ is the rotation matrix of the target posture of the surgical actuator, i.e. the posture matrix included in the target posture 302 of the surgical actuator; $p_c$ is the current position of the surgical actuator, i.e. the position vector contained in the current posture 305 of the surgical actuator; $R_c$ is the rotation matrix of the current posture of the surgical actuator, i.e. the posture matrix included in the current posture 305 of the surgical actuator; $v_{lim}$ the linear velocity limitation of the surgical actuator, i.e. artificially-set parameter; $\omega_{lim}$ is the angular velocity limitation of the surgical actuator, i.e. artificially-set parameter; $rot_{\hat{r}}^{-1}(R_t R_c^T)$ is the unit vector of the rotational axis required to rotate from the current posture of the surgical actuator to the target posture of the surgical actuator; $\hat{r}$ denotes that the $rot_{\hat{r}}^{-1}(R_t R_c^T)$ is a unit vector;

4) using the robotic forward kinematics model to calculate, by the controlling computer 202, the current position 308 of the sheath relative to the outer sleeve according to the joint position values 303 of the multi-degree-of-freedom mechanical arm, the bending angle value 304 of the sections of the flexible surgical tool and the spatial position 307 of the sheath, the spatial position 307 of the sheath is a spatial position where the sheath is fixed to the surgical incision;

5) obtaining the motion limitation condition 309 applied by the sheath to the outer sleeve based on the current position 308 of the sheath relative to the outer sleeve; according to the motion limitation condition 309 and the desired velocity 306 of the surgical actuator, applying inverse kinematics algorithm with multi-priority-object to calculate the joint velocity 311 of the multi-degree-of-freedom mechanical arm and the bending velocity 312 of the sections of the flexible surgical tool;

the motion limitation condition 309 is that the velocity of the outer sleeve 105 at a particular fixed point in the sheath 103 or sheath 108 (i.e. the intersection point of the channel axis for passing through the outer sleeve 105 in the sheath 103 or sheath 108 with the skin incision) shall be consistent with the tangential direction of the channel axis for passing through the outer sleeve 105 at the particular fixed point so as to ensure that the motion of the outer sleeve 105 will not make the sheath 103 pull the surgical incision;

6) calculating a target joint position value 313 of the multi-degree-of-freedom mechanical arm based on the joint velocity 311 of the multi-degree-of-freedom mechanical arm and a preset control loop time 315, and transmitting the same to the controller of the multi-degree-of-freedom mechanical arm 101 to drive the individual joints;

7) calculating a target bending angle value 314 of the sections of the flexible surgical tool according to the bending velocity 312 of the sections of the flexible surgical tool and the control loop time 315, and transmitting it to the controller of the flexible surgical tool 102 to drive the respective sections;

8) ending the control loop and repeating the actions from step 1) to step 7).

In the above step 5), the inverse kinematics algorithm 310 with the multi-priority-object is as follows:

$$C=H\dot{q} \quad C=v_{RCM\perp}=0$$

$$\dot{x}=J\dot{q}$$

$$\dot{q}=(I-H^+H)(J(I-H^+H))+\dot{x}$$

In the formula, C is the motion limitation condition; H is the Jacobian matrix of the motion limitation condition; $\dot{q}$ is a vector consisting of the joint velocity 311 of the multi-degree-of-freedom mechanical arm and the bending velocity 312 of the sections of the flexible surgical tool; $v_{RCM\perp}$ is a velocity vector in a direction at which the outer sleeve is at a particular fixed point in the sheath 103 or sheath 108, the direction is the tangential direction of the particular fixed point that is perpendicular to the axis line of the outer sleeve 105; $\dot{x}$ is the desired velocity vector for the surgical actuator 107 (i.e. the desired velocity of the surgical actuator); J is the Jacobian matrix for surgical actuator 107.

The inverse kinematics algorithm 310 with the multi-priority-object is an inverse kinematics operation with an improved Jacobian matrix obtained by combining the Jacobian matrix of the surgical actuator 107 with the Jacobian matrix with motion limitation conditions, which not only satisfies the motion limitation conditions applied by the sheath to the outer sleeve, but also ensures the achievement of the desired velocity 306 of the surgical actuator.

The above embodiments are merely illustrative of the present invention, and the structure, size, arrangement position and shape of each component may be varied. On the basis of the technical solution of the present invention, the improvements or equivalent transformations made to individual components according to the principles of the present invention should not be excluded from the scope of protection of the present invention.

The invention claimed is:

1. A computer for controlling a flexible surgical tool system, the flexible surgical tool system comprising a multi-degree-of-freedom mechanical arm, a flexible surgical tool, and a remote control device, the flexible surgical tool comprising an outer sleeve and a surgical actuator, and the computer being configured to:
  receive a status signal of the remote control device;
  calculate a target posture of the surgical actuator;
  obtain a current posture of the surgical actuator based on joint position values of the multi-degree-of-freedom mechanical arm and a bending angle value of the flexible surgical tool;
  calculate a target velocity of the surgical actuator according to the target posture and the current posture of the surgical actuator;
  calculate a current position of a sheath relative to the outer sleeve according to the joint position values of the multi-degree-of-freedom mechanical arm, the bending angle value of the flexible surgical tool, and a spatial position of the sheath;
  obtain a motion limitation condition applied by the sheath to the outer sleeve based on the current position of the sheath relative to the outer sleeve;
  calculate a target joint position value of the multi-degree-of-freedom mechanical arm based on the motion limitation condition and the target velocity of the surgical actuator; and
  calculate a target bending angle value of the flexible surgical tool based on the motion limitation condition and the target velocity of the surgical actuator.

2. The computer of claim 1, further configured to apply an inverse kinematics algorithm with multi-priority-object to calculate a joint velocity of the multi-degree-of-freedom mechanical arm and a bending velocity of the flexible surgical tool according to the motion limitation condition and the target velocity of the surgical actuator.

3. The computer of claim 2, further configured to:
  calculate the target joint position value of the multi-degree-of-freedom mechanical arm based on the joint velocity of the multi-degree-of-freedom mechanical arm and a preset control loop time; and
  calculate the target bending angle value of the flexible surgical tool according to the bending velocity of the flexible surgical tool and the preset control loop time.

4. The computer of claim 1, further configured to apply a robotic forward kinematics model to obtain the current posture of the surgical actuator or calculate the current position of the sheath relative to the outer sleeve.

5. The computer of claim 1, further configured to:
  transmit the target joint position value of the multi-degree-of-freedom mechanical arm to the multi-degree-of-freedom mechanical arm; and
  transmit the target bending angle value of the flexible surgical tool to the flexible surgical tool.

6. The computer of claim 1, wherein the target velocity of the surgical actuator is calculated as follows:

$$\dot{x} = \begin{bmatrix} v \\ \omega \end{bmatrix} = \begin{bmatrix} v_{lim}(p_t - p_c)/\|p_t - p_c\| \\ \omega_{lim} rot_r^{-1}(R_t R_c^T) \end{bmatrix},$$

wherein, $\dot{x}$ is the velocity vector of the surgical actuator, including a linear velocity vector v and an angular velocity vector $\omega$; $p_t$ is the target position of the surgical actuator, $R_t$, is the rotation matrix of the target posture of the surgical actuator, $p_c$ is the current position of the surgical actuator, $R_c$ is a rotation matrix of the current posture of the surgical actuator, $v_{lim}$ is the linear velocity limitation value of the surgical actuator; $\omega_{lim}$ is the angular velocity limitation value of the surgical actuator; $rot_{\hat{r}}^{-1}(R_t R_c^T)$ is the unit vector of the rotational axis required to rotate from the current posture of the surgical actuator to the target posture of the surgical actuator; $\hat{r}$ denotes that the $rot_{\hat{r}}^{-1}(R_t R_c^T)$ is a unit vector.

7. The computer of claim 1, wherein the spatial position of the sheath is a spatial position where the sheath is fixed to a surgical incision.

8. The computer of claim 1, wherein the motion limitation condition is a condition in which a velocity direction of the outer sleeve at a particular fixed point in the sheath is consistent with a tangential direction of a channel axis for passing through the outer sleeve at the particular fixed point, and the particular fixed point is an intersection point of the channel axis for passing through the outer sleeve in the sheath with a skin incision.

9. The computer of claim 2, wherein the inverse kinematics algorithm with the multi-priority-object is:

$$C = H\dot{q} \quad C = v_{RCM\perp} = 0$$

$$\dot{x} = J\dot{q}$$

$$\dot{q} = (I - H^+ H)(J(I - H^+ H)) + \dot{x}$$

wherein, C is a motion limitation condition; H is the Jacobian matrix of the motion limitation condition; $\dot{q}$ is a vector consisting of the joint velocity of the multi-degree-of-freedom mechanical arm and the bending velocity of the sections of the flexible surgical tool; $v_{RCM\perp}$ is a velocity vector in a direction at which the outer sleeve is at a particular fixed point in the sheath, the direction is the tangential direction of the particular fixed point that is perpendicular to the channel axis of the outer sleeve; $\dot{x}$ is the desired velocity vector for the surgical actuator; J is the Jacobian matrix for surgical actuators.

10. A flexible surgical tool system, comprising:
a multi-degree-of-freedom mechanical arm;
a flexible surgical tool comprising an outer sleeve and a surgical actuator;
a remote control device configured to transmit a status signal; and
a computer configured to:
   receive a status signal from the remote control device;
   calculate a target posture of the surgical actuator;
   obtain a current posture of the surgical actuator based on joint position values of the multi-degree-of-freedom mechanical arm and a bending angle value of the flexible surgical tool;
   calculate a target velocity of the surgical actuator according to the target posture and the current posture of the surgical actuator;
   calculate a current position of a sheath relative to the outer sleeve according to the joint position values of the multi-degree-of-freedom mechanical arm, the bending angle value of the flexible surgical tool and a spatial position of the sheath;
   obtain a motion limitation condition applied by the sheath to the outer sleeve based on the current position of the sheath relative to the outer sleeve;
   calculate a target joint position value of the multi-degree-of-freedom mechanical arm based on the motion limitation condition and the target velocity of the surgical actuator; and
   calculate a target bending angle value of the flexible surgical tool based on the motion limitation condition and the target velocity of the surgical actuator.

11. The flexible surgical tool system of claim 10, wherein the computer is further configured to apply an inverse kinematics algorithm with multi-priority-object to calculate a joint velocity of the multi-degree-of-freedom mechanical arm and a bending velocity of the flexible surgical tool according to the motion limitation condition and the target velocity of the surgical actuator.

12. The flexible surgical tool system of claim 11, wherein the computer is further configured to:
   calculate the target joint position value of the multi-degree-of-freedom mechanical arm based on the joint velocity of the multi-degree-of-freedom mechanical arm and a preset control loop time; and
   calculate the target bending angle value of the flexible surgical tool according to the bending velocity of the flexible surgical tool and the preset control loop time.

13. The flexible surgical tool system of claim 10, wherein the computer is further configured to apply a robotic forward kinematics model to obtain the current posture of the surgical actuator or calculate the current position of the sheath relative to the outer sleeve.

14. The flexible surgical tool system of claim 10, wherein the computer is further configured to:
   transmit the target joint position value of the multi-degree-of-freedom mechanical arm to the multi-degree-of-freedom mechanical arm; and
   transmit the target bending angle value of the flexible surgical tool to the flexible surgical tool.

15. The flexible surgical tool system of claim 10, wherein the velocity of the surgical actuator is calculated as follows:

$$\dot{x} = \begin{bmatrix} v \\ \omega \end{bmatrix} = \begin{bmatrix} v_{lim}(p_t - p_c)/\|p_t - p_c\| \\ \omega_{lim} rot_{\hat{r}}^{-1}(R_t R_c^T) \end{bmatrix},$$

wherein, $\dot{x}$ is the velocity vector of the surgical actuator, including a linear velocity vector v and an angular velocity vector $\omega$; $p_t$ is the target position of the surgical actuator, i.e. the position vectors included in the target posture of the surgical actuator; $R_t$ is the rotation matrix of the target posture of the surgical actuator, i.e., the posture matrix included in the target posture of the surgical actuator; $p_c$ is the current position of the surgical actuator, i.e., the position vector included in the current posture of the surgical actuator; $R_c$ is a rotation matrix of the current posture of the surgical actuator, i.e., the posture matrix included in the current posture of the surgical actuator; $v_{lim}$ is the linear velocity limitation value of the surgical actuator; $\omega_{lim}$ is the angular velocity limitation value of the surgical actuator; $rot_{\hat{r}}^{-1}(R_t R_c^T)$ is the unit vector of the rotational axis required to rotate from the current posture of the surgical actuator to the target posture of the surgical actuator; $\hat{r}$ denotes that the $rot_{\hat{r}}^{-1}(R_t R_c^T)$ is a unit vector.

16. The flexible surgical tool system of claim 10, wherein the motion limitation condition is a condition in which a velocity direction of the outer sleeve at a particular fixed point in the sheath is consistent with a tangential direction of a channel axis for passing through the outer sleeve at the particular fixed point, and the particular fixed point is an intersection point of the channel axis for passing through the outer sleeve in the sheath with a skin incision.

17. The flexible surgical tool system of claim 11, wherein the inverse kinematics algorithm with the multi-priority-object is:

$$C = H\dot{q} \quad C = v_{RCM\perp} = 0$$

$$\dot{x} = J\dot{q}$$

$$\dot{q} = (I - H^+ H)(J(I - H^+ H)) + \dot{x}$$

wherein, C is a motion limitation condition; H is the Jacobian matrix of the motion limitation condition; $\dot{q}$ is a vector consisting of the joint velocity of the multi-degree-of-freedom mechanical arm and the bending velocity of the sections of the flexible surgical tool; $v_{RCM\perp}$ is a velocity vector in a direction at which the outer sleeve is at a particular fixed point in the sheath, the direction is the tangential direction of the particular fixed point that is perpendicular to the channel axis of the outer sleeve; $\dot{x}$ is the desired velocity vector for the surgical actuator; J is the Jacobian matrix for surgical actuators.

18. The flexible surgical tool system of claim 10, wherein:
the computer is further configured to:
receive a current status fed back by the multi-degree-of-freedom mechanism arm and the flexible surgical tool, the current status comprising motion postures of the multi-degree-of-freedom mechanical arm and the flexible surgical tool and information about an encountered external disturbance;
process the received current status; and
transmit processed information to the remote control device; and
the remote control device is further configured to:
output an acting force to reflect a latent degree of a motion of the multi-degree-of-freedom mechanical arm and the flexible surgical tool or the information about the encountered external disturbance.

19. The flexible surgical tool system of claim 10, wherein the multi-degree-of-freedom mechanical arm comprises:
a mechanical arm controller connected to the computer through an Ethernet and connected to a motor driver through a controller LAN bus; and
a plurality of rotation angle sensors for detecting the joint position values of the multi-degree-of-freedom mechanical arm in real time.

20. The flexible surgical tool system of claim 10, wherein the flexible surgical tool further comprises:
a flexible surgical tool controller connected to the computer through an Ethernet and connected to a motor driver through a controller LAN bus, the flexible surgical tool controller being configured to execute a forward kinematic algorithm to obtain the bending angle value of the flexible surgical tool; and
a plurality of rotation angle sensors configured to measure a rotation angle: of an output axis of a motor in the flexible surgical tool in real time.

* * * * *